(12) United States Patent
Deville

(10) Patent No.: US 8,791,054 B2
(45) Date of Patent: Jul. 29, 2014

(54) METHODS OF CONVERTING AN INACTIVE BIOCIDE INTO AN ACTIVE BIOCIDE USING A CHEMICAL REACTION

(71) Applicant: Halliburton Energy Services, Inc., Houston, TX (US)

(72) Inventor: Jay P. Deville, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 22 days.

(21) Appl. No.: 13/629,506

(22) Filed: Sep. 27, 2012

(65) Prior Publication Data

US 2014/0087978 A1    Mar. 27, 2014

(51) Int. Cl.
  *C09K 8/528* (2006.01)
  *C09K 8/64* (2006.01)
(52) U.S. Cl.
  USPC ........... 507/237; 507/240; 507/244; 507/254; 507/262; 507/263; 507/266; 507/267; 507/268
(58) Field of Classification Search
  None
  See application file for complete search history.

(56) References Cited

U.S. PATENT DOCUMENTS

| 6,503,449 B1 * | 1/2003 | Smith ............................. 422/20 |
| 7,712,534 B2 | 5/2010 | Bryant et al. |
| 2003/0057401 A1 * | 3/2003 | Craig ............................ 252/387 |
| 2004/0120853 A1 * | 6/2004 | Carpenter et al. ............... 422/37 |
| 2010/0160449 A1 * | 6/2010 | Rovison et al. ............... 514/714 |

FOREIGN PATENT DOCUMENTS

| WO | WO 0004777 A1 * | 2/2000 |
| WO | WO 0132224 A1 | 5/2001 |
| WO | WO 2010115735 A2 | 10/2010 |

OTHER PUBLICATIONS

Scenihr, Assessment of the Antibiotic Resistance Effects of Biocides, European Commission, Directorate-General for Health & Consumers, Jan. 19, 2009.

* cited by examiner

*Primary Examiner* — John J Figueroa
(74) *Attorney, Agent, or Firm* — Craig W. Roddy; Sheri Higgins Law; Sheri Higgins

(57) ABSTRACT

A method of converting an inactive biocide into an active biocide comprises: contacting the inactive biocide with an activating agent, wherein the activating agent is capable of chemically reacting with the inactive biocide; and causing or allowing a chemical reaction to take place between the inactive biocide and the activating agent, wherein the chemical reaction produces the active biocide. The methods can also include deactivating the active biocide via a chemical reaction between the active biocide and a deactivating agent.

20 Claims, No Drawings

METHODS OF CONVERTING AN INACTIVE BIOCIDE INTO AN ACTIVE BIOCIDE USING A CHEMICAL REACTION

TECHNICAL FIELD

Methods of converting an inactive biocide into an active biocide are provided. The inactive biocide is converted to the active biocide via a chemical reaction between the inactive biocide and an activating agent. The chemical reaction can be a reduction-oxidation reaction or a reaction with an acid or a base. According to an embodiment, the active biocide is converted back to an inactive biocide after use via a chemical reaction between the active biocide and a deactivating agent. According to certain embodiments, the active biocide is used in an oil or gas operation.

SUMMARY

According to an embodiment, a method of converting an inactive biocide into an active biocide comprises: contacting the inactive biocide with an activating agent, wherein the activating agent is capable of chemically reacting with the inactive biocide; and causing or allowing a chemical reaction to take place between the inactive biocide and the activating agent, wherein the chemical reaction produces the active biocide.

DETAILED DESCRIPTION OF THE INVENTION

As used herein, the words "comprise," "have," "include," and all grammatical variations thereof are each intended to have an open, non-limiting meaning that does not exclude additional elements or steps.

As used herein, a "fluid" is a substance having a continuous phase that tends to flow and to conform to the outline of its container when the substance is tested at a temperature of 71° F. (22° C.) and a pressure of one atmosphere "atm" (0.1 megapascals "MPa"). A fluid can be a liquid or gas. A homogenous fluid has only one phase; whereas a heterogeneous fluid has more than one distinct phase. A colloid is an example of a heterogeneous fluid. A colloid can be: a slurry, which includes a continuous liquid phase and undissolved solid particles as the dispersed phase; an emulsion, which includes a continuous liquid phase and at least one dispersed phase of immiscible liquid droplets; a foam, which includes a continuous liquid phase and a gas as the dispersed phase; or a mist, which includes a continuous gas phase and liquid droplets as the dispersed phase.

Biocides are commonly used in a variety of industries, including, medicine, agriculture, forestry, and oil and gas. A "biocide" is a chemical substance or microorganism which can destroy, deter, render harmless, or exert a controlling effect on another organism by chemical or biological means. Biocides can be added to other materials (typically liquids) in order to protect the material against biological infestation and growth. Some chemical biocides are synthetic. Biocides that are microorganisms include several types of bacteria. Biocides are also used as anti-fouling agents and disinfectants.

In the oil and gas industry, biocides can be included in a treatment fluid that is introduced into a well. A well can include, without limitation, an oil, gas or water production well, an injection well, or a geothermal well. As used herein, a "well" includes at least one wellbore. A wellbore can include vertical, inclined, and horizontal portions, and it can be straight, curved, or branched. As used herein, the term "wellbore" includes any cased, and any uncased, open-hole portion of the wellbore. A near-wellbore region is the subterranean material and rock of the subterranean formation surrounding the wellbore. As used herein, a "well" also includes the near-wellbore region. The near-wellbore region is generally considered to be the region within approximately 100 feet of the wellbore. As used herein, "into a well" means and includes into any portion of the well, including into the wellbore or into the near-wellbore region via the wellbore.

A portion of a wellbore may be an open hole or cased hole. In an open-hole wellbore portion, a tubing string may be placed into the wellbore. The tubing string allows fluids to be introduced into or flowed from a remote portion of the wellbore. In a cased-hole wellbore portion, a casing is placed into the wellbore which can also contain a tubing string. A wellbore can contain an annulus. Examples of an annulus include, but are not limited to: the space between the wellbore and the outside of a tubing string in an open-hole wellbore; the space between the wellbore and the outside of a casing in a cased-hole wellbore; and the space between the inside of a casing and the outside of a tubing string in a cased-hole wellbore. In order to produce oil or gas, a wellbore is drilled into a reservoir or adjacent to a reservoir. A subterranean formation containing oil or gas is sometimes referred to as a reservoir. A reservoir may be located under land or off shore.

Treatment fluids used in the oil and gas industry commonly include essential additives and other substances. Often times, the additives and other substances are composed of polymers. Some microorganisms that can be present in the well, can consume the additives and other substances present in the fluid. If the additive is consumed, then the additive is no longer present in the treatment fluid to perform the necessary function. When a microorganism consumes an additive or a substance, the microorganism can flourish, which can foul the treatment fluid and create an unpleasant smell. Moreover, some microorganisms can produce hydrogen sulfide gas ($H_2S$) extracellularly during consumption. It is undesirable for a well to contain high amounts of a sour gas, such as hydrogen sulfide gas (commonly called a sour gas well). A sour gas is considered to be a corrosive substance. If a fluid in a well contains a corrosive substance, then the fluid might be detrimental to wellbore operations, for example, harmful to wellbore equipment, such as pumping equipment or pipes. Therefore, it is often desirable to include a biocide in a treatment fluid. The biocide can function to destroy or deter the microorganism from consuming the additives or other substances in a treatment fluid.

However, safety concerns often arise when storing, transporting, or handling biocides. Because biocides are intended to destroy living organisms, many biocidal products pose significant risk to human health and welfare. As such, protective clothing and special equipment is often required when handling biocides. Moreover, the use of biocides can have significant adverse effects on areas surrounding the area of use. For example, if a biocide is accidentally spilled on the ground, then the biocide can adversely affect plants and animals in the area of the spill.

Therefore, there is a need for a superior way to safely store, transport, and handle biocides. There is also a need for the biocide to be capable of functioning as a biocide at the desired time.

It has been discovered that an inactive biocide can be safely stored, transported, and handled. The inactive biocide can then be converted into an active biocide at a desired time.

According to an embodiment, a method of converting an inactive biocide into an active biocide comprises: contacting the inactive biocide with an activating agent, wherein the activating agent is capable of chemically reacting with the inactive biocide; and causing or allowing a chemical reaction to take place between the inactive biocide and the activating agent, wherein the chemical reaction produces the active biocide.

As used herein, the phrase "inactive biocide" means a biocide that contains a substantial portion that is incapable of functioning as a biocide to destroy, deter, render harmless, or exert a controlling effect on another organism by chemical or biological means. As used herein, the phrase "active biocide" means a biocide that contains a substantial portion that is capable of functioning as a biocide to destroy, deter, render harmless, or exert a controlling effect on another organism by chemical or biological means. As used herein, the term "substantial" means a value in the range of about 55% to 100%. It is to be understood that an inactive biocide may include a portion that is capable of functioning as a biocide, but the active portion should not be so great that the inactive biocide as a whole is capable of causing adverse affects to organisms. It is also to be understood that an active biocide may include a portion that is incapable of functioning as a biocide, but the inactive portion should not be so great that the active biocide as a whole is incapable of causing adverse affects to organisms. The biocidal strength of one biocide can be stronger than another biocide. Therefore, the percentage making up the substantial portion of an inactive biocide may need to be higher (e.g., >90%) for a stronger biocide and can be lower (e.g., 60%) for a weaker biocide. Moreover, the percentage making up the substantial portion of an active biocide can be lower (e.g., 60%) for a stronger biocide and may need to be higher (e.g., >90%) for a weaker biocide. One of skill in the art, will be able to determine the percentage of the inactive and active portions for a particular biocide depending on the strength of that biocide.

The inactive biocide can be an oxidized biocide. The oxidized biocide can be formed via a reduction-oxidation (redox) reaction in which the biocide becomes oxidized. As used herein, the term "oxidized," and all grammatical variations thereof, means the loss of electrons or an increase in the oxidation state of the molecule. As used herein, the term "molecule" means an electrically-neutral group of two or more atoms held together by covalent chemical bonds, wherein the two or more atoms can be the same or different. Examples of oxidized biocides include, but are not limited to, tetrakishydroxymethyl phosphonium sulfate (THPS) oxide, glutaric acid, 2-bromo-2-nitropropane-1,3-dial (oxidized bronapol), and oxidized dazomet (dazomet N-oxide or dazomet sulfoxide).

The inactive biocide can also be a reduced biocide. The reduced biocide can be formed via a redox reaction in which the biocide becomes reduced. As used herein, the term "reduced," and all grammatical variations thereof, means the gain of electrons or a decrease in the oxidation state of the molecule. An example of a reduced biocide is 1,6-hexanediol.

According to an embodiment, the inactive biocide can be stored, transported, and handled without the need for special safety equipment or precautions.

The activating agent is capable of chemically reacting with the inactive biocide. The methods include the step of causing or allowing a chemical reaction to take place between the inactive biocide and the activating agent, wherein the chemical reaction produces the active biocide. According to an embodiment, the chemical reaction is a reduction-oxidation (redox) reaction. According to another embodiment, the chemical reaction is a reaction between the inactive biocide and an acid or a base.

The activating agent can be any molecule that is capable of chemically reacting with the inactive biocide to form the active biocide. The activating agent can be a reducing agent. According to an embodiment, the activating agent is a reducing agent when the inactive biocide is an oxidized biocide. In this manner, during the redox reaction between the activating agent and the inactive biocide, the activating agent transfers electrons to the inactive biocide, and the activating agent becomes oxidized and the inactive biocide becomes reduced. The reduction of the inactive biocide produces the active biocide. An example according to this embodiment is when a redox reaction between the inactive biocide tetrakishydroxymethyl phosphonium sulfate (THPS) oxide and the reducing agent sodium borohydride produces the active biocide THPS and borane. The reducing agent can be, for example, a sulfite, an erythorbate, an ascorbate, or a hydride-based reducing agent.

According to an embodiment, the activating agent has a strength such that harmful effects to the environment and dangers to workers do not occur during the chemical reaction between the inactive biocide and the activating agent. By way of example, a strong reducing agent can produce hydrogen gas during the chemical reaction with an oxidized molecule. Hydrogen gas is a highly flammable substance, and as such, the presence of the gas can pose safety concerns to workers.

The activating agent can also be an oxidizing agent. According to an embodiment, the activating agent is an oxidizing agent when the inactive biocide is a reduced biocide. In this manner, during the redox reaction between the activating agent and the inactive biocide, the activating agent takes electrons from the inactive biocide, and the activating agent becomes reduced and the inactive biocide becomes oxidized. Examples of oxidizing agents include, but are not limited to, perborates, persulfates, silver ions, hypochlorites, and (2,2,6,6-Tetramethylpiperidin-1-yl)oxyl, or (2,2,6,6-tetramethylpiperidin-1-yl)oxidanyl "TEMPO" radicals. The oxidation of the inactive biocide produces the active biocide. An example according to this embodiment is when a redox reaction between the inactive biocide 1,6-hexandiol and the oxidizing agent persulfate produces the active biocide glutaraldehyde and a sulfate.

The activating agent can also be an acid or a base. According to an embodiment, the inactive biocide can be selected such that the chemical reaction between the inactive biocide and the acid or base, and possibly other reactants (e.g., water) form the active biocide. An example according to this embodiment is when the inactive biocide gluteraldehyde dimethyl acetal, chemically reacts with an acid and water to produce the active biocide gluteraldehyde. The reaction with the acid or the base can also be, for example, an acid or base-catalyzed hydrolysis of an ester. The hydrolysis of an ester can produce an active biocide of an alcohol or carboxylic acid.

It is to be understood that there are other chemical reactions, other than redox reactions and reactions with an acid or base, that could convert the inactive biocide into an active biocide, and the aforementioned examples are not intended to limit the scope of the invention.

The active biocide can be an oxidizing biocide or a non-oxidizing biocide. The active biocide can be, without limitation, organic and inorganic acids, esters and salts; biguanides; aldehydes; alcohols; peroxygens; derivatives of 1,3-dioxane; derivatives of imidazole; derivatives of hexamine; and isothiazolones. According to an embodiment, the active biocide is selected from the group consisting of tetrakishydroxymethyl phosphonium sulfate (THPS); glutaraldehyde (pentanedial); formaldehyde (methanal); ortho-phthalaldehyde; formic acid; acetic acid (ethanoic acid); propionic acid; undecanoic acid (undecylenic acid); 2,4-hexadienoic acid (sorbic acid); lactic acid; benzoic acid; salicylic acid; dehydroacetic acid (DHA, 3-acetyl-6-methylpyran-2,4[3H]-dione); sulphur dioxide; sulphites; bisulphites; esters of p-hydroxybenzoic acid (parabens); including methyl paraben, ethyl paraben, propyl paraben, and butyl paraben; vanillic acid esters; chlorhexidine; alexidine; polymeric biguanides; ethyl alcohol (ethanol); methyl alcohol (methanol); isopropyl alcohol (isopropanol); benzyl alcohol; phenylethanol (phenylethyl alcohol); bronopol[13] (2-bromo-2-nitro-1,3-diol); phenoxyethanol (phenoxetol); chlorbutanol (chlorbutol); 2,4-dichlorobenzyl alcohol; hydrogen peroxide; peracetic acid; 2,6-dimethyl-1,3-dioxan-4-ol acetate (isomeric mixture) (dimethoxane); 5-bromo-5-nitro-1,3-dioxane (Bronidox); 1,3-di-hydroxymethyl-5,5-dimethyl-2,4-dioxoimidazole; 1,3-di-hydroxymethyl-5,5-dimethylhydantoin (Dantoin); N,N"-methylene bis[5'[1-hydroxymethyl]-2,5-dioxo-4-imidazolidinyl urea] (Germall 115); diazolidinyl urea; a mixture of 5-chloro-2-methyl-4-isothiazolin-3-one (CMIT) and 2-methyl-4-isothiazolin-3-one (MIT); 2-methyl-4-isothiazolin-3-one (MIT); 2-n-octyl-4-isothiazolin-3-one; 1,2-benzisothiazolin-3-one (BIT); and combinations thereof. According to an embodiment, if there is to be more than one active biocide, then each of the inactive biocides chemically react with the activating agent via the same type of chemical reaction. For example, it is preferred that each of the inactive biocides chemically react via a redox reaction to produce the active biocides. According to this example, each of the inactive biocides would produce its respective active biocide by being oxidized during the redox reaction, by being reduced, etc.

The active biocide can be used for a variety of applications including, disinfectant, wastewater treatment, corrosion inhibitor, scale dispersant, anti-fouling agent, fungicide, germicide, herbicide, insecticide, and saponification. The specific active biocide can vary and be selected depending on the specific application. The specific active biocide can also be selected based on the specific organism(s) to be controlled via the active biocide. By way of example, in the oil and gas industry, active biocides can be used to prevent microbial growth of aerobic and anaerobic bacteria. Therefore, the exact active biocide can be selected to prevent growth of specific organisms in a well.

The methods can further include the step of adding the inactive biocide to a fluid, wherein the step of adding can be performed simultaneously with, or prior to, the step of contacting the inactive biocide with the activating agent. The fluid can also include the activating agent. The methods can also include the step of adding the activating agent to the fluid. According to another embodiment, the activating agent is included in a second fluid, and the methods can further include the step of adding the activating agent to the second fluid. The inactive biocide and the activating agent can be in a solid form, for example a powder. The inactive biocide and the activating agent can also be included in a liquid form. Any of the fluids can be a solution wherein the inactive biocide or the activating agent is a solute and a liquid is the solvent. The fluid can also be a colloid. The colloid can be: a slurry wherein the dispersed phase comprises the inactive biocide or the activating agent and a liquid is the continuous phase; a slurry wherein the continuous phase comprises the inactive biocide or the activating agent and a liquid; an emulsion wherein the dispersed phase or the continuous phase comprises the inactive biocide or the activating agent; or a foam wherein the continuous phase comprises the inactive biocide or the activating agent. The fluid can be an aqueous-based fluid or a hydrocarbon-based fluid. As used herein, the phrase "aqueous-based" means the fluid comprises an aqueous liquid and the phrase "hydrocarbon-based" means the fluid comprises a hydrocarbon liquid. The fluid can be a wellbore treatment fluid for use in an oil or gas operation. According to an embodiment, the inactive biocide is included in a first wellbore treatment fluid. The first wellbore treatment fluid can also include the activating agent or the activating agent can be included in a second wellbore treatment fluid. The wellbore treatment fluids can be, without limitation, a drilling fluid, a spacer fluid, a completion fluid, a work-over fluid, a stimulation fluid (e.g. a fracturing fluid or acidizing fluid), a packer fluid, or a cement composition. The wellbore treatment fluid(s) can be any fluid used to treat at least a portion of a well or subterranean formation.

The methods include the step of causing or allowing a chemical reaction to take place between the inactive biocide and the activating agent, wherein the chemical reaction produces the active biocide. The step of causing can be performed after the step of adding the inactive biocide and the activating agent to a fluid. The step of causing can also be performed after the step of introducing the first wellbore treatment fluid into the well. The step of causing can include contacting the inactive biocide and the activating agent with a catalyst. The catalyst can cause the chemical reaction to take place between the inactive biocide and the activating agent to produce the active biocide or the catalyst can also increase the rate of the chemical reaction.

The methods can further include the step of introducing the first wellbore treatment fluid into a well, wherein the step of introducing is performed after the step of adding the inactive biocide to a fluid. The step of causing or allowing a chemical reaction to take place between the inactive biocide and the activating agent can also be performed after the step of introducing the first wellbore treatment fluid into the well. The step of introducing can also be performed prior to the step of contacting the inactive biocide with the activating agent. The well can be, without limitation, an oil, gas, or water producing well, an injection well, or a geothermal well. If the activating agent is included in the second treatment fluid, then the step of contacting the inactive biocide with the activating agent can comprise introducing the second treatment fluid into the portion of the well that contains the first treatment fluid. The activating agent can also be included in a fluid that is already present in the well. According to this embodiment, the step of contacting can include allowing the first wellbore treatment fluid to come in contact with the fluid that contains the activating agent.

The methods can further include the step of causing or allowing a chemical reaction to take place between the active biocide and a deactivating agent, wherein the chemical reaction produces an inactive biocide, and wherein the step of causing or allowing a chemical reaction to take place between the active biocide and a deactivating agent can be performed after the step of causing or allowing a chemical reaction to take place between the inactive biocide and the activating agent. The step of causing or allowing a chemical reaction to take place between the active biocide and a deactivating agent can also be performed after the step of introducing the first, and optionally the second, wellbore treatment fluids into the well. The methods can further include the step of allowing the active biocide to remain in an active state for a desired period of time. The desired period of time can be the time wherein biocidal functionality is needed.

According to an embodiment, the chemical reaction between the active biocide and the deactivating agent is a reduction-oxidation (redox) reaction. According to another embodiment, the chemical reaction is a reaction between the active biocide and an acid or a base, and possibly other reactants (e.g., water).

The deactivating agent can be any molecule that is capable of chemically reacting with the active biocide to form an inactive biocide. The deactivating agent can be a reducing agent, an oxidizing agent, a base, or an acid. Preferably, the deactivating agent is the opposite of the activating agent. For example, if the activating agent is a reducing agent, then the deactivating agent can be an oxidizing agent; and if the activating agent is an acid, then the deactivating agent can be a base. The methods can further include the step of adding the deactivating agent to a fluid. The discussion of suitable fluids and properties is discussed above. The methods can further include the step of introducing a source of oxygen into the well. The step of introducing the oxygen source can include aerating the first treatment fluid. The deactivation of the active biocide can be useful, for example, when the fluid containing the active biocide is to be stored, transported, or handled after the desired use of the active biocide. By way of example, it is not uncommon for wellbore treatment fluids to be returned to the wellhead whereby the fluids are re-used, stored, or transported to another location. By having the active biocide deactivated, safety issues are no longer a concern. The methods can further include the step of removing at least a portion of the first treatment fluid from the well.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is, therefore, evident that the particular illustrative embodiments disclosed above may be altered or modified and all such variations are considered within the scope and spirit of the present invention. While compositions and methods are described in terms of "comprising," "containing," or "including" various components or steps, the compositions and methods also can "consist essentially of" or "consist of" the various components and steps. Whenever a numerical range with a lower limit and an upper limit is disclosed, any number and any included range falling within the range is specifically disclosed. In particular, every range of values (of the form, "from about a to about b," or, equivalently, "from approximately a to b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an", as used in the claims, are defined herein to mean one or more than one of the element that it introduces. If there is any conflict in the usages of a word or term in this specification and one or more patent(s) or other documents that may be incorporated herein by reference, the definitions that are consistent with this specification should be adopted.

What is claimed is:

1. A method of converting an inactive biocide into an active biocide comprising:
   contacting the inactive biocide with an activating agent, wherein the activating agent is capable of chemically reacting with the inactive biocide; and
   causing or allowing a chemical reaction to take place between the inactive biocide and the activating agent, wherein the chemical reaction produces the active biocide.

2. The method according to claim 1, wherein the chemical reaction is a reduction-oxidation reaction or an acid-base reaction.

3. The method according to claim 2, wherein the inactive biocide is an oxidized biocide or a reduced biocide.

4. The method according to claim 3, wherein the oxidized biocide is formed via a reduction-oxidation reaction in which the biocide becomes oxidized.

5. The method according to claim 4, wherein the oxidized biocide is selected from the group consisting of tetrakishydroxymethyl phosphonium sulfate oxide, glutaric acid, 2-bromo-2-nitropropane-1,3-dial, oxidized dazomet, and combinations thereof.

6. The method according to claim 3, wherein the reduced biocide is formed via a reduction-oxidation reaction in which the biocide becomes reduced.

7. The method according to claim 6, wherein the reduced biocide is 1,6-hexanediol.

8. The method according to claim 3, wherein the activating agent is a reducing agent, an oxidizing agent, a base, or an acid.

9. The method according to claim 8, wherein the activating agent is a reducing agent when the inactive biocide is an oxidized biocide.

10. The method according to claim 8, wherein the activating agent is an oxidizing agent when the inactive biocide is a reduced biocide.

11. The method according to claim 8, wherein the activating agent is a base, and the inactive biocide chemically reacts with at least the activating agent to produce the active biocide.

12. The method according to claim 8, wherein the activating agent is an acid, and the inactive biocide chemically reacts with at least the activating agent to produce the active biocide.

13. The method according to claim 1, wherein the active biocide is selected from the group consisting of: organic and inorganic acids, esters and salts; biguanides; aldehydes; alcohols; peroxygens; derivatives of 1,3-dioxane; derivatives of imidazole; derivatives of hexamine; isothiazolones; and combinations thereof.

14. The method according to claim 13, wherein the active biocide is selected from the group consisting of tetrakishydroxymethyl phosphonium sulfate; glutaraldehyde; formaldehyde; ortho-phthalaldehyde; formic acid; acetic acid; propionic acid; undecanoic acid; 2,4-Hexadienoic acid; lactic acid; benzoic acid; salicylic acid; dehydroacetic acid; sulphur dioxide; sulphites; bisulphites; esters of p-hydroxybenzoic acid; including methyl paraben, ethyl paraben, propyl paraben, and butyl paraben; vanillic acid esters; chlorhexidine; alexidine; polymeric biguanides; ethyl alcohol; methyl alcohol; isopropyl alcohol; benzyl alcohol; phenylethyl alcohol; 2-bromo-2-nitro-1,3-diol; phenoxyethanol; chlorbutanol; 2,4-dichlorobenzyl alcohol; hydrogen peroxide; peracetic acid; 2,6-dimethyl-1,3-dioxan-4-ol acetate; 5-bromo-5-nitro-1,3-dioxane; 1,3-di-hydroxymethyl-5,5-dimethyl-2,4-dioxoimidazole; 1,3-di-hydroxymethyl)-5,5-dimethylhydantoin; N,N"-methylene bis[5'[1-hydroxymethyl]-2,5-dioxo-4-imidazolidinyl urea]; diazolidinyl urea; a mixture of 5-chloro-2-methyl-4-isothiazolin-3-one and 2-methyl-4-isothiazolin-3-one; 2-methyl-4-isothiazolin-3-one; 2-n-octyl-4-isothiazolin-3-one; 1,2-benzisothiazolin-3-one; and combinations thereof.

15. The method according to claim 1, further comprising the step of adding the inactive biocide to a fluid, wherein the step of adding is performed simultaneously with, or prior to, the step of contacting the inactive biocide with the activating agent.

16. The method according to claim 15, wherein the fluid further comprises the activating agent.

17. The method according to claim 15, wherein the fluid is a wellbore treatment fluid for use in an oil or gas operation.

18. The method according to claim 17, further comprising the step of introducing the wellbore treatment fluid into a well, wherein the step of introducing is performed after the step of adding the inactive biocide to the fluid.

19. The method according to claim 18, wherein the well is an oil, gas, or water production well, an injection well, or a geothermal well.

20. The method according to claim 1, further comprising the step of causing or allowing a chemical reaction to take place between the active biocide and a deactivating agent, wherein the chemical reaction produces an inactive biocide, and wherein the step of causing or allowing a chemical reaction to take place between the active biocide and a deactivating agent is performed after the step of causing or allowing a chemical reaction to take place between the inactive biocide and the activating agent.

* * * * *